United States Patent [19]

Parsonage et al.

[11] Patent Number: 5,338,430
[45] Date of Patent: Aug. 16, 1994

[54] NANOSTRUCTURED ELECTRODE MEMBRANES

[75] Inventors: Edward E. Parsonage, Minneapolis; Mark K. Debe, Stillwater, both of Minn.

[73] Assignee: Minnesota Mining and Manufacturing Company, St. Paul, Minn.

[21] Appl. No.: 995,891

[22] Filed: Dec. 23, 1992

[51] Int. Cl.$^5$ .......................................... G01N 27/26
[52] U.S. Cl. .................... 204/412; 204/414; 204/415; 204/416; 204/418; 204/419; 204/421; 204/424; 204/426
[58] Field of Search .............. 204/412, 414, 415, 416, 204/418, 419, 421, 424, 426; 429/31, 33, 34, 36, 40, 41, 46

[56] References Cited

U.S. PATENT DOCUMENTS

| | | | |
|---|---|---|---|
| 3,045,198 | 7/1962 | Dolan et al. | 338/13 |
| 3,969,545 | 7/1976 | Slocum | 427/163 |
| 4,132,616 | 1/1979 | Tantram et al. | 204/195 P |
| 4,148,294 | 4/1979 | Scherber et al. | 126/270 |
| 4,155,781 | 5/1979 | Diepers | 148/175 |
| 4,169,779 | 10/1979 | Tataria et al. | 204/195 P |
| 4,209,008 | 6/1980 | Lemkey et al. | 126/452 |
| 4,224,595 | 9/1980 | Dolan | 338/13 |
| 4,252,864 | 2/1981 | Coldren | 428/571 |
| 4,324,632 | 4/1982 | Tamtram et al. | 204/195 P |
| 4,347,732 | 9/1982 | Leary | 73/23 |
| 4,396,643 | 8/1983 | Kuehn et al. | 427/160 |
| 4,474,648 | 10/1984 | Tantram et al. | 204/1 T |
| 4,587,003 | 5/1986 | Tantram et al. | 204/412 |
| 4,633,704 | 1/1987 | Tantram et al. | 73/23 |
| 4,674,320 | 6/1987 | Hirschfeld | 73/23 |
| 4,795,543 | 1/1989 | Stetter et al. | 204/412 |
| 4,812,352 | 3/1989 | Debe | 428/142 |
| 4,847,594 | 7/1989 | Stetter | 340/540 |
| 4,865,717 | 9/1989 | Setter et al. | 204/415 |
| 4,873,970 | 10/1989 | Freidank et al. | 128/202.22 |
| 4,969,545 | 11/1990 | Hayashi | 192/0.076 |
| 5,039,561 | 8/1991 | Debe | 427/255.6 |
| 5,069,987 | 12/1991 | Gordon | 429/34 |

FOREIGN PATENT DOCUMENTS

| | | |
|---|---|---|
| 4041143C1 | of 0000 | Fed. Rep. of Germany . |
| 4-43951 | 2/1992 | Japan . |
| 1101101 | 1/1968 | United Kingdom . |
| 1200595 | 7/1970 | United Kingdom . |
| 1571282 | 9/1980 | United Kingdom . |
| 2094005A | 9/1982 | United Kingdom . |

OTHER PUBLICATIONS

J. Vac. Sci. Technol. A 1 (3), Jul.–Sep. 1983, "Ion-bombardment-induced whisker formation on graphite", J. A. Floro et al. pp. 1398–1402.

Organic Chemistry, Third Ed., Allyn and Bacon, Inc. Chapters 30 and 31. No month and year presently available.

SPIE vol. 1637, Environmental and Process Monitoring Technologies (1992) "Optical Sensors in Environmental Applications" pp. 270–279. No month presently available.

Sensors and Actuators B, 7 (1992) 609 613, Gutierrez et al. "Design of polycrystalline gas sensors based on ad-

(List continued on next page.)

*Primary Examiner*—John Niebling
*Assistant Examiner*—Bruce F. Bell
*Attorney, Agent, or Firm*—Gary L. Griswold; Walter N. Kiirn; Carolyn V. Peters

[57] ABSTRACT

A nanostructured composite film comprising a plurality of nanostructured elements, wherein the nanostructured elements are either two-component sub-microscopic structures comprised of whiskers conformally coated with a conducting, preferentially catalytically active material or one component sub-microscopic structures comprised of a conducting preferentially catalytically active material, such that the nanostructured elements are embedded in an encapsulant, wherein the encapsulant can be a solid electrolyte. The composite film can be used as an electrode membrane in an electrochemical cell or sensor.

26 Claims, 4 Drawing Sheets

OTHER PUBLICATIONS mittance spectrum measurements". No month presently available.

Sensors and Actuators B, 7 (1992) 614–618, L. M. Lechuga et al. "Different catalytic metals (Pt., Pd and Ir) for GaAs Schottky barrier sensors". No month presently available.

Sensors and Actuators B, 8 (1992) 161–166, M. Archensault et al. "A simple intrinsic optical-fibre chemical sensor". No month presently available.

Sensors and Actuators, 19 (1989) 33–40, He–Qing et al. "Solid Polymer Electrolyte-Based Electrochemical Oxygen Sensor". No month presently available.

Sensors and Actuators, 31 (1990) 319–325, Otagawa et al. "Planar Microelectrochemical Carbon Monoxide Sensors". No month presently available.

1981 American Chemical Society, A. B. LaConti et al., pp. 551–573 "Recent Developments in Electrochemical Solid Polymer Electrolyte Sensor Cells for Measuring Carbon Monoxide and Oxides of Nitrogen".

Sensors and Actuators, 4, 32 (1992) 313–317, P. Bruschi et al. "Sensing properties of polypyrrole-polytetrafluoroethylene composite thin films from granular metal-polymer precursors".

Sensors and Actuators, B1 (1990) 303–307, Buttner et al. "An Integrated Amperometric Microsensor".

1986 American Chemical Society, Fundamentals and Applications of Chemical Sensors, Nov. 18, 1985, pp. 202–214.

Science, vol. 258, Nov. 20, 1992, Zuburtikudis et al. "Linear Metal Nanostructures and Size Effects of Supported Metal Catalysts".

Electrochemical Methods Fundamentals and Applications, Bard and Faulkner (John Wiley & Sons).

NANOSTRUCTURED ELECTRODE MEMBRANES

TECHNICAL FIELD

This invention relates to electrochemical devices such as sensors, fuel cells and batteries, and in particular to electrode membranes used in such devices.

BACKGROUND OF THE INVENTION

The electrochemical sensors can be divided into those utilizing high temperature nonporous, inorganic electrolytes and those using gas permeable low temperature electrolytes. Of the latter category a further division can be made according to whether the electrolyte is a solid polymer on one hand, or a liquid, paste or gel on the other.

A typical solid polymer electrolyte (SPE) based electrochemical sensor has at least a working (sometimes referred to as a sensing electrode) and counter electrodes in contact with an SPE. A reference electrode may also be used to form a 3-electrode device. The electrode material, preferably a metal with catalytic properties, is typically Au, Pt, Pd or noble metals and their alloys in the form of wire grids, powders or films.

Various structures and means have been used to apply or otherwise bring a catalyst in contact with an electrolyte to form working, counter, and reference electrodes. The electrode membrane constructions can be summarized as: (a) solid metal films in contact with the SPE, (b) porous metal films or planar distributions of metal particles deposited on top of the SPE or powders pressed against an SPE surface, (c) metal grids or meshes deposited on top of the SPE or embedded within an SPE layer, or (d) separate sheets of catalyst particles bonded in Teflon, which are pressed against the SPE.

Examples of such an known electrode membrane constructions include:

(1) metal (Pt) films formed by electroless chemical plating directly onto Nation TM membrane surfaces;

(2) porous Pt layers chemically plated onto a Nation TM film, forming a network of interconnected islands of Pt particles interspersed with roughly circular regions (40–100 μm diameter) of Nation TM film containing little or no platinum; and (3) Pt discs spin coated with Nation TM solution followed by electrodeposited ruthenium ad-atoms onto a Nation TM film.

Examples of metal grid or mesh based electrodes include:

(1) membrane electrodes with a conducting layer of contiguous metal particles deposited by vacuum evaporation on, and adhering to a non-porous material, overcoated with a permeable membrane layer;

(2) porous 100 nm thick Au films vacuum vapor deposited on to Nation TM films;

(3) grid electrode membranes has been produced by vacuum evaporation of Au onto Nation TM substrates through photolithographically etched masks, followed by spin coating Nation TM solutions over such electrode configurations; the length-to-width ratio of the grid wires being varied;

(4) thin film electrode Nation TM film structures constructed by sputtering Pt through photolithographically etched masks onto various substrates and overcoating the Pt electrodes with various Nation TM films coated from solution;

(5) ultrafine grid structures made by photolithographically etching 30 nm thick Au films previously deposited on oxidized Si wafers, and after etching, spin coating with Nation TM solutions; and (6) multiple electrodes, biased to null out environmental effects, formed on a common substrate by depositing a metal film and overcoating with a Nation TM membrane.

Examples of electrode membranes wherein catalyst particles are pressed onto an SPE include:

(1) Pt and Ag powders pressed to the sides of SPEs made of compacted discs of Teflon TM and zirconium phosphate powders and antimonic oxide powders;

(2) metal powders pressed into Nation TM sheet surfaces, and contacted with a gold mesh;

(3) catalyzed carbon black loaded into the surface of Nation TM membranes and placed in contact with carbon black loaded Teflon membranes;

(4) a gold minigrid (500 wires/inch) mechanically pressed into the surface of a Nation TM film, followed by "gluing" the pressed minigrid to the membrane by solution casting a further layer of Nation TM solution over the assembly since the mechanical pressing tends not to give good contact by itself; and (5) Pt wire meshes partially hot pressed into a Nation TM surface.

Other examples of electrode membranes include:

(1) electrodes comprised of hydrophobic Teflon TM - bonded Pt black layers pressed against Nation TM membranes; and (2) electrodes pressed against Nation TM membranes, the electrodes being fabricated from platinoid black and Pt-5% Ir catalyst compositions blended with a Teflon TM binder.

Processes for bonding a catalytic material coated onto a current collecting screen and embedding it into the surface of a polymeric cation exchange membrane and other basic processes and properties of an electrode formed of a mixture of noble metal particles bonded with hydrophobic materials have been described.

While the art known electrode membranes have proven useful, such electrode membranes constructed from vapor coated grids and metal films tend to suffer several severe mechanical problems, delamination and cracking as a result of swelling and shrinkage of the SPE, especially when exposed to humidity. Such problems contribute to a decrease in signal from the electrodes with time over and above changes due to catalytic site effects. The adhesion of vapor deposited noble metal films to polymers tends to be poor, thus requiring an adhesion promoting layer like Cr to be deposited first, which can lead to corrosion and degradation of the electrode membrane upon use. Furthermore, the pressed metal meshes generally suffer delamination problems as known in the art.

SUMMARY OF THE INVENTION

The present invention is directed to electrochemical sensors either using solid electrolytes or a liquid, paste or gel electrolyte, and more specifically demonstrates advances over the art using solid polymer electrolytes (SPE). Among the advantages of SPE-based sensors over liquid or gel type sensors are their freedom from leakage and packaging corrosion, and adaptability to size reduction, such as for making "microsensors."

Briefly, in one aspect of the present invention, a nanostructured composite film is provided comprising a plurality of nanostructured elements, wherein the nanostructured elements are sub-microscopic two-component structures comprised of whiskers conformally coated with a conducting, preferentially catalytically active material and an encapsulating polymer.

In another aspect of the present invention, a nanostructured electrode membrane is provided comprising a plurality of nanostructured elements, wherein the nanostructured elements comprise whiskers optionally coated with a conductive material embedded in an encapsulating solid electrolyte.

In another aspect, a nanostructured composite film is provided comprising a plurality of nanostructured elements, wherein the nanostructured elements are sub-microscopic electrically conductive, preferentially catalytically active single component structures embedded in an encapsulant.

Another aspect of this invention is the method for fabricating the electrode/membrane, which when used with solid electrolytes improves processing efficiency, thus allowing large sheets of the electrode membrane to be produced economically. Further, the new process is environmentally friendly because the process eliminates the solvent casting step that can be used to coat the nanostructured elements.

The nanostructured composite film (NCF) of the present invention and process of fabrication have several advantages over art known electrode membrane designs.

In contrast to the art known electrode membrane designs, the nanostructured elements of the NCFs are automatically protected because they are substantially discrete (separated) and buried or embedded just under the surface. Embedding the nanostructured elements beneficially protects them from abrasive forces.

A second advantage of the nanostructured electrode membranes of the present invention is that significantly less electrically conductive material is required for the same or larger sensitivity than for art known designs. Art known grid constructions profess to use significantly less (50 to 375 times less) catalytic or electrically conductive material than more conventional metal powder/bonded Teflon TM electrodes. However, these grid constructions still employ a significant fraction of the catalyst or conductive material in bulk form, often functioning as a support for the surface metal.

In contrast, the nanostructured elements used in the present invention preferably comprise an inert core coated with a thin electrically conductive coating, and as such the elements have a much larger fraction of the coating material's volume contributing to the surface active area, and much less is required since the inert core is the support for the conducting catalyst coating.

For example, the ultrafine gold grid sensors of Butther (Sensors and Material 2 (1990)90) use 0.2 mg/19 mm² or ~1000 μg/cm². On the other hand, nanostructured electrode membranes of the present invention typically use a mass equivalent thickness of 100 nm to 200 nm of metal applied to the planar area of the whiskers, giving a coating thickness of ~10 nm on the sides of the whiskers since the geometric area of the nanostructured whiskers is 10–15 times the planar area for 1–2 μm tall and 0.05 μm wide nanostructured elements. This amounts to only ~2 μg/cm² of gold, which is 500 times less than the finest grid (50 micrometer holes) electrode structure of the art and ~$10^5$ times less than used by conventional sensors with metal powder bonded Teflon TM electrodes.

Further, in the present invention relatively small amounts of the coating material can nucleate into nanoscopic islands on the sides of the inert core of the nanostructured elements to produce a large increase in true molecular adsorption surface area, with measured BET $N_2$ values indicating an increase in surface area on the order of 3000.

Advantageously, the process of the present invention for fabrication of the nanostructured composite films is conducive to large area coated web production means, making the electrode membranes more economical. The nanostructured composite films can be fabricated either in a batch process or by continuous web processes. Once the nanostructured elements have been constructed, the elements can be embedded in the encapsulant by coating the nanostructured elements and then curing the encapsulant. Alternatively, the nanostructured elements can be embedded by hot roll calendering them into a solid polymer surface. Continuous web processes result in large sheets of nanostructured membrane media, which can be cut, shaped, and folded as required.

Another advantage is that the geometric shape, size and distribution of the nanostructured elements embedded in the surface of the encapsulant gives the nanostructured membrane significantly enhanced catalytic activity. This results in enhanced sensitivity for detection of gases and vapors.

The enhanced sensitivity derives from many of the same factors that suggest the perpendicularly oriented acicular shaped nanostructured elements are preferred in the nanostructured layer. The electrochemically generated current per unit planar area of electrode (S) is proportional to the total catalytically active surface area per unit area accessible to both the electrolyte and analytes. This total surface area is proportional to the product of the number (N) of nanostructured elements per unit area and the geometric area (A) of each nanostructured elements, $S = \alpha NA$, wherein $\alpha$ is proportionality constant.

For example, if the elements have length (l) and radius (r) and are oriented perpendicular to the surface, then the number per unit planar area of surface is $N \leq 1/(4r^2)$, each having a surface area $A = 2\pi rl$, then $S_\perp = \alpha \pi l/2r$. In contrast, if the particles were oriented parallel to the surface, $N \leq 1/(2rl)$ and $S_\parallel = \alpha\pi$. So, $S_\perp/S_\parallel = 1/2r \gg 1$, it is preferable to have the acicular particles oriented perpendicular to the surface.

Similarly, it can be deduced that it is preferable to have acicular nanostructured elements with $1/r$ large rather than more spherical particles with $l \approx r$, since again $S_{acic}/S_{sph} = 1/2r$.

Finally, it is known to those in the art of catalysis that the surface of very small particles is more catalytically active than the surface of bulk-like metal. By having the conductive coating present as a discontinuous coating on the whiskers, the catalytic material is in a form more advantageous for catalytic activity, as well, as presenting a further increase in surface area for adsorption of the electrochemical species.

Definitions as used in this application:
"acicular" means having an aspect ratio of $\geq 3$;
"aspect ratio" means a ratio of an element's height to its average cross-sectional width;

"discrete" means distinct elements, having a separate identity, but does not preclude elements from being in contact with one another;

"nanostructured element" means an acicular, discrete, oriented, sub-microscopic, preferably a two-component structure comprised of a whisker coated with an electrically conductive material; alternatively, the nanostructured element may be a one-component structure wherein the electrically conductive material only forms the discrete, oriented structure;

"nanostructured composite film" means a film containing nanostructured elements embedded in an encapsulant, wherein the encapsulant may contain an electrolyte; "nanostructured composite film" includes a "nanostructured electrode membrane";

"nanostructured electrode membrane" means a film containing nanostructured elements in an encapsulant, wherein the encapsulant is an electrolyte-containing polymer and the membrane may be configured for either a two-electrode or three-electrode sensor;

"oriented" includes random or uniaxial;

"solid electrolyte" includes non polymeric materials of a solid consistency that will allow ionic conductivity;

"solid polymer electrolyte" includes polymer materials of a solid consistency that will allow ionic conductivity;

"submicroscopic" means having at least one dimension smaller than approximately a micrometer; and "whisker" means the inert core of the nanostructured element.

DESCRIPTION OF THE PREFERRED EMBODIMENT(S)

Electrochemical devices typically comprise three primary components, (i) a gas, liquid or solid material that is consumed in an electrochemical (EC) reaction, (ii) two electrically conducting catalyst electrode membranes on which surfaces the EC reactions take place, and (iii) an electrolyte to conduct ionic charge and reaction products between opposing electrodes. A fourth component (iv) may be a permeation limiting film controlling transport of the consumed material to the catalyst surface. It is known in the art that the EC reaction requires the presence of the three components (i–iii) to be mutually contiguous and that optimizing the mutual conjunction of these three components will optimize the device performance. More specifically this invention describes a new geometric structure for the catalyst electrode material (ii), which when incorporated intimately into a solid polymer electrolyte (iii) or film (iv) offers a number of advantages over the prior arts' means for forming the electrode membrane (E/M), including optimization of the three component interface. Further aspects of this invention teach different ways to incorporate this new catalyst electrode structure (ii) into components (iii) and (iv) to form useful EC sensors, fuel cells and batteries.

Figure 4:
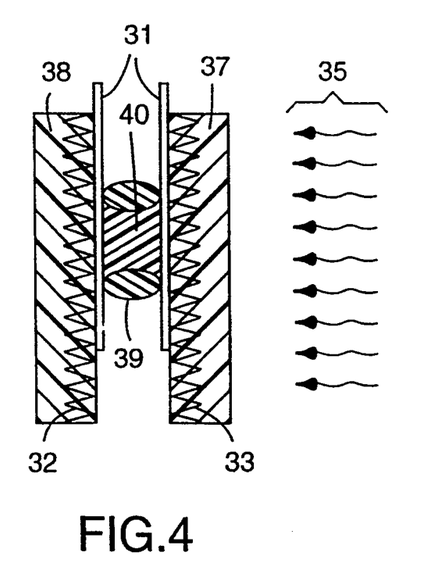
FIG. 4 is a schematic of an alternative two-electrode sensor according to the present invention.
Figure 5:
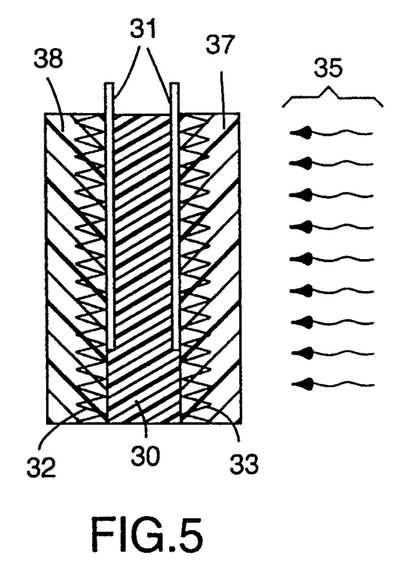
FIG. 5 is a schematic of an alternative two-electrode sensor according to the present invention.

The catalyst membrane structure is comprised of nanostructured composite films (NCF), generally described in U.S. patent application 07/720,188, filed Jun. 24, 1991. Contemplated to be within the scope of the present invention are various electrochemical cell configurations using the electrode membrane structures of the present invention. The electrode membrane structures have been categorized to illustrate the present invention. Among the various configurations contemplated are the following non-limiting examples:

(1) The membrane structure may be fabricated such that an electrochemical cell could use at least two pieces of a nanostructured composite film in combination with a solid polymer electrolyte film or an electrolyte paste. Such constructions are illustrated in FIGS. 4 and 5. Referring to FIGS. 4 and 5 an electrochemical cell (configured as a electrochemical sensor) is schematically illustrated. A working electrode is comprised of a first encapsulant (37) wherein a first set of nanostructured elements (33) are embedded therein. A counter electrode is comprised of a second encapsulant (38) wherein a second set of nanostructured elements (32) are embedded therein. A conductive wire (31) is adhered to the conductive surface of the two electrodes and is connected to a measurement device and/or a power source. Positioned between and in intimate contact with the electrochemically active surface is either an electrolyte paste (40) or a solid polymer electrolyte (30). When an electrolyte paste (40) is used, a retaining means (39) is used to keep the paste in position. The figure illustrates an O-ring (39). The analyte (represented by 35) is sensed through the working electrode. Typically, the first and second encapsulants have a permeability differential, wherein the encapsulant of the counter electrode has a lower permeability than the working electrode. Typically, the first and second sets of nanostructured elements are coated with different electrically conductive materials, although this is not required. Other various coatings and enclosures can also be used.

(2) An electrochemical cell could be constructed using at least two pieces of a nanostructured composite film wherein the nanostructured elements are embedded in a solid polymer electrolyte. In such an instance, the film pieces could be laminated together with the electrochemically active surface of the film pieces opposite each other, that is, the electrochemically active surfaces face outward. Counter and working electrodes could be fabricated using different solid polymers. Furthermore, the nanostructured elements can be coated with different electrically conductive materials.

(3) An electrochemical cell could be constructed using at least two pieces of a nanostructured composite film wherein the nanostructured elements embedded in a solid polymer electrolyte are laminated together with the active surface of the films facing outward and separated from each other with an ionically conductive material, for example a solid polymer electrolyte or an electrolyte paste. Counter and working electrodes could be fabricated using different solid polymers. Furthermore, the nanostructured elements can be coated with different electrically conductive materials.

Figure 2:
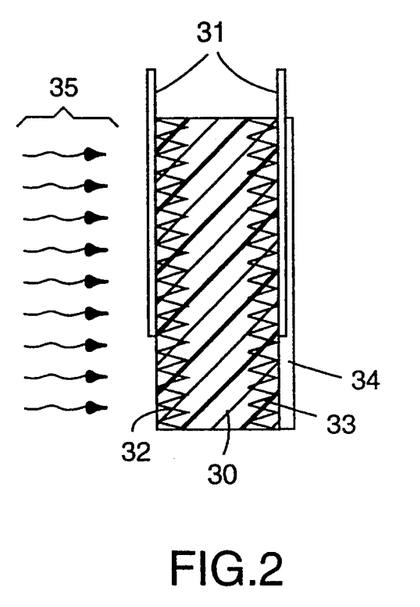
FIG. 2 is a schematic of a two-electrode sensor according to the present invention.

(4) FIGS. 2 and 3 illustrate yet another contemplated configuration for an electrochemical cell. Referring to FIG. 2 an electrochemical cell (configured as a electrochemical sensor) is schematically illustrated. A working electrode is comprised of a first set of nanostructured elements (33) embedded in a solid polymer electrolyte (30). A counter electrode is comprised of a second set of nanostructured elements (32) embedded in the solid polymer electrolyte (30) on the surface opposite the first set of nanostructured elements (33). A conductive wire (31) is adhered to the conductive surface of the two electrodes. The analyte (represented by 35) is sensed through the working electrode. The counter electrode is shielded from the analyte (35) by an optional impermeable layer (34), in this illustration, a piece of tape. The first and second sets of nanostructured elements may be coated with different electrically conductive materials, although this is not required.

Figure 3:
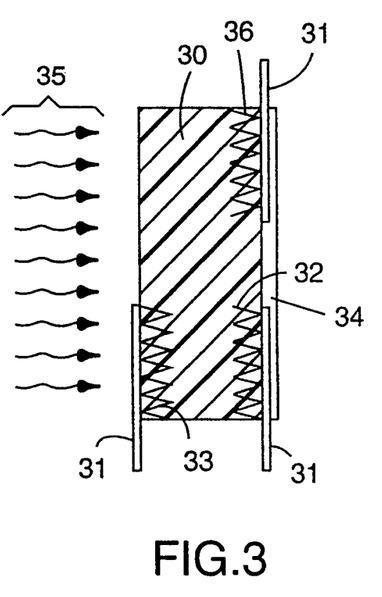
FIG. 3 is a schematic of a three-electrode sensor according to the present invention.

Referring to FIG. 3, a three-electrode electrochemical cell is illustrated comprising a working electrode comprised of a first set of nanostructured elements (33) embedded in a solid polymer electrolyte (30). A reference electrode is comprised of a second set of nanostructured elements (32) embedded in the solid polymer electrolyte (30) on the surface opposite the first set of nanostructured elements (33). Preferably, these two sets of nanostructured elements are directly opposed to each other on the common solid polymer electrolyte. A counter electrode is comprised of a third set of nanostructured elements (36) embedded in the solid polymer electrolyte (30) on the same surface as the reference electrode, but above or to the side of the second set of nanostructured elements (32). A conductive wire (31) is adhered to the conductive surface of the two electrodes. The analyte (represented by 35) is sensed through the working electrode. The counter electrode is shielded from the analyte (35) by an impermeable layer (34), in this illustration, a piece of tape. The first, second and third sets of nanostructured elements may be coated with different electrically conductive materials, although this is not required. Although a specific arrangement of the 3-electrodes is illustrated, other configuration could also be used.

In the preferred embodiment of the present invention, the electrically conductive material can be incorporated directly at the surface of an electrolyte in an optimized geometric structural form. This geometric structural form provides advantages over art known structures. The optimized geometric structural form is a very dense array of acicular (large length/width ratio), discrete, oriented submicroscopic elements. Two-component elements, consisting of conducting, preferably catalytic material coated around an inert core whisker, have lengths of ~1–5 micrometers ($\mu m$), diameters ~0.05–0.1 $\mu m$, orientations substantially parallel to one another with long axes normal to the polymer surface, and number densities of 3 to 4 billion per $cm^2$. Single phase elements can also be used, although the two-phase elements are preferred. These single phase elements have dimensions similar to the two phase elements, however, the single phase elements consist only of an electrically conductive material.

The nanostructured elements can be randomly or uniaxially oriented. Perferably, the elements are uniaxially oriented because this orientation allows the close packing to be optimized, thereby increasing the surface area available for reaction per unit area of membrane. The shape, orientation, size and numbers of elements optimizes the surface area for EC reactions. Coating the electrically conductive material around (conformally) (refer to FIG. 1a) the inert core whisker further maximizes the surface area while minimizing the amount of coating material needed. Coating this material such that it consists of small rough particles covering the sides of the inert core whisker (refer to FIGS. 1 and 1(a)) further increases the surface area for reaction, even over the conformally coated whiskers.

A process for making the nanostructured composite film used to demonstrate this invention is described in U.S. Pat. No. 5,238,729 and such description is incorporated herein by reference. Particularly useful nanostuctured elements comprising the nanostructured composite film are described in U.S. Pat. No. 4,812,352 and such description is incorporated herein by reference.

Figure 1:
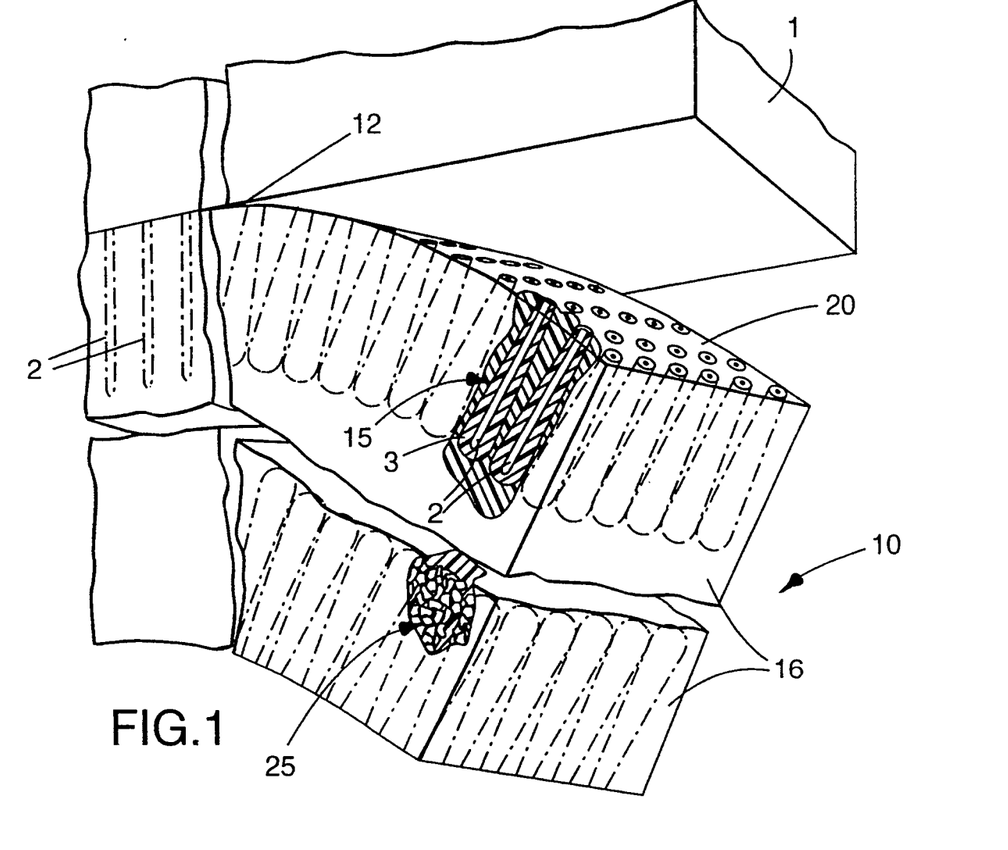
FIG. 1 is a perspective view of an electrode membrane of the present invention.
Figure 1A:
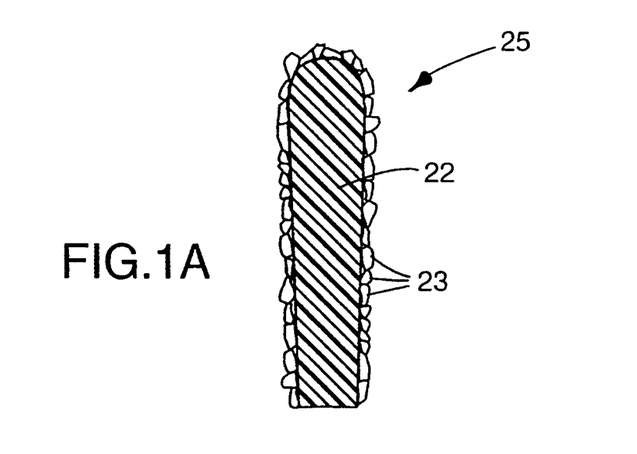
FIG. 1a is a cross-sectional view of a nanostructured element having a discontinuous conformal coating.

Referring to FIG. 1, nanostructured composite film (10) is comprised of high aspect ratio whiskers (2) comprised of an organic pigment grown such that their long axes are perpendicular to a temporary substrate (1), such as copper-coated polyimide. Whiskers (2) are discrete, oriented normal to substrate (1), predominantly noncontacting, have cross-sectional dimensions on the order of 0.05 $\mu m$ or less, lengths of 1–2 $\mu m$ and areal number densities of approximately 40–50/$\mu m^2$. Whiskers (2) are then coated with a thin shell (3) of an electrically conductive material, for example, by vacuum evaporation or sputter deposition. Nanostructured elements (15) are then embedded into an encapsulant (16). Typically, to construct an electrochemical cell, at least one "set" of nanostructured elements are embedded in the encapsulant (16). One set of elements are on one major surface, while the other set of elements are embedded on the opposite side, that is, the other major surface of the solid polymer, as illustrated. Nanostructured composite film (10) (referred to as "film") is then peeled from temporary substrate (1), cleanly carrying nanostructured elements (15) along, embedded on one surface of film (10), thereby exposing the electrochemically active surface (20) of nanostructured composite film (10). Encapsulant (16) can be (a) a solid electrolyte film, (b) a film former or (c) a solid solution or mixture of a polymer and an electrolyte.

Materials useful as temporary substrate (1) for the present invention include those which maintain their integrity at the temperatures and pressures imposed upon them during any deposition and annealing steps of subsequent materials applied to the temporary substrate. The temporary substrate may be flexible or rigid, planar or non-planar, convex, concave, aspheric or any combination thereof.

Preferred temporary substrate materials include organic or inorganic materials, such as, polymers, metals, ceramics, glasses, and semiconductors. The preferred organic substrate is metal-coated polyimide film (commercially available from DuPont Corp. under the trade designation KAPTON). Additional examples of substrate materials appropriate for the present invention can be found and described in U.S. Pat. No. 4,812,352 and such description is incorporated herein by reference.

Starting materials useful in preparing whiskers (2) include organic and inorganic compounds. Whiskers (2) are essentially a non-reactive or passive matrix for the subsequent thin metal coating and encapsulant. Several techniques or methods are useful for producing the whisker-like configuration of the particles. Such methods for making inorganic-, metallic-, or semiconductor-based microstructured-layers or whisker-like structures are described in J. Vac. Sci. Tech. A 1983, 1(3), 1398–1402; U.S. Pat. Nos. 4,969,545; 4,252,864; 4,396,643; 4,148,294; 4,155,781; and 4,209,008, and such descriptions are incorporated herein by reference.

Useful organic compounds include planar molecules comprising chains or rings over which $\pi$-electron density is extensively delocalized. These organic materials generally crystallize in a herringbone configuration. Preferred organic materials can be broadly classified as polynuclear aromatic hydrocarbons and heterocyclic aromatic compounds. Polynuclear aromatic hydrocarbons are described in Morrison and Boyd, *Organic Chemistry*, 3rd ed., Allyn and Bacon, Inc. (Boston, 1974), Chap. 30. Heterocyclic aromatic compounds are described in Chap. 31 of the same reference.

Preferred polynuclear aromatic hydrocarbons include, for example, naphthalenes, phenanthrenes, perylenes, anthracenes, coronenes, and pyrenes. A preferred polynuclear aromatic hydrocarbon is N,N'-di(3,5-xylyl)perylene-3,4:9,10 bis(dicarboximide) (commercially available from American Hoechst Corp. under the trade designation of "C.I. Pigment Red 149") [hereinafter referred to as perylene red].

Preferred heterocyclic aromatic compounds include, for example, phthalocyanines, porphyfins, carbazoles, purines, and pterins. More preferred heterocyclic aromatic compounds include, for example, porphyrin, and phthalocyanine, and their metal complexes, for example, copper phthalocyanine (commercially available from Eastman Kodak).

The organic material used to produce whiskers may be coated onto a temporary substrate using well-known techniques in the art for applying a layer of an organic material onto a substrate including but not limited to vacuum evaporation, sputter coating, chemical vapor deposition, spray coating, Langmuir-Blodgett, or blade coating. Preferably, the organic layer is applied by physical vacuum vapor deposition (i.e., sublimation of the organic material under an applied vacuum). The preferred temperature of the temporary substrate during deposition is dependent on the organic material selected. For perylene red, a substrate temperature near room temperature (i.e., about 25° C.) is satisfactory.

In a particularly useful method for generating organic whiskers, the thickness of the deposited organic layer will determine the major dimension of the microstructures which form during an annealing step. Whiskers are grown on a temporary substrate with the characteristics and process described in U.S. Pat. No. 5,039,561, and such descriptions are incorporated herein by reference. An alternative process for generating the whiskers includes depositing a whisker generating material on a temporary substrate wherein the whisker generating material and the temporary substrate are at an elevated temperature. Material is then deposited until high aspect ratio randomly-oriented whiskers are obtained. The preferred process for obtaining the perylene red whiskers includes depositing the whisker generating material at or near room temperature and then elevating the substrate temperature to anneal the whisker generating material (described in Example 1 hereinbelow).

In both instances, perylene red is the organic material preferred. When the organic material is perylene red, the thickness of the layer (when using the preferred process), prior to annealing is in the range from about 0.05 to about 0.25 $\mu$m, more preferably in the range of 0.05 to 0.15 $\mu$m. When the organic materials are annealed, generally uniaxially-oriented whiskers are produced. Preferably, the whiskers are monocrystalline or polycrystalline rather than amorphous. The properties, both chemical and physical, of the layer of whiskers are anisotropic due to the crystalline nature and uniform orientation of the nanostructured elements.

Typically, the orientation of the whiskers is uniformly related to the temporary substrate surface. The whiskers are preferably substantially uniaxially-oriented normal to the temporary substrate surface, that is, perpendicular to the temporary substrate surface. The major axes of the whiskers are generally parallel to one another. The whiskers are typically uniform in size and shape, and have uniform cross-sectional dimensions along their major axes. The preferred length of each whisker is in the range of 0.1 to 2.5 $\mu$m, more preferably in the range of 0.5 to 1.5 $\mu$m. The diameter or cross-sectional width of each whisker is preferably less than 0.1 $\mu$m.

The whiskers preferably have a high aspect ratio, (i.e., length of the whisker to diameter or cross-sectional width of the whisker ratio is in the range from about 3:1 to about 100:1). The major dimension of each whisker is directly proportional to the thickness or amount of the initially deposited organic material. The areal number densities of the conformally coated nanostructured elements are preferably in the range of 40–50/$\mu$m$^2$.

The nanostructured elements, submicrometer in width and a few micrometers in length, are composites comprising whiskers conformally coated with a thin electrically conductive material coating. In addition to providing an electrically conductive coating material, the coating material will generally strengthen the nanostructured elements. The electrically conductive material can be fully conformally coated over the whiskers, producing a generally smooth thin shell around the whiskers (refer to FIG. 1). Alternatively, this material can be discontinuously conformally coated such that it consists of small rough particles coveting the sides of the whiskers (refer to FIG. 1a) further increasing the surface area available for reaction, even over the fully conformally coated whiskers. Generally, the conductive coating material is selected to optimize the electrochemical reaction being sensed. Preferably, the conductive coating material is catalytically active and selected from the group consisting of conducting metals, semi-metals and semiconductors. Such materials include Cr, Co, Ir, Ni, Pd, Pt, Au, Ag, Cu, Be, Mg, Sc, Y, La, Ti, Zr, Hf, V, Nb, Ta, Mo, W, Mn, Tc, Re, Fe, Ru, Os, Rh, Zn, Cd, Hg, B, Al, Ga, In, Tl, C, Si, Ge, Sn, Pb, As, Sb, Bi, Se, Te and alloys thereof, such as CrCo, NiCr, PtIr. The wall thickness of the coating material surrounding the whiskers is in the range from about 0.5 nm to about 50 nm. The thickness of the coating material may be such that the resulting nanostructured elements remain substantially discrete although there may be substantial contact between the elements.

The coating material may be deposited onto the whiskers using conventional techniques, including, for example, those described in U.S. Pat. No. 5,238,729, supra. Preferably, the coating material is deposited by a method that avoids the disturbance or destruction of the whiskers by mechanical or mechanical-like forces. More preferably, the coating material is deposited by vacuum deposition methods, such as, vacuum sublimation, sputtering, vapor transport, and chemical vapor deposition.

Essentially, compared to the art known grid surfaces contacting an SPE, the nanostructured elements provide a three dimensionally distributed enhanced surface area which is potentially all available for catalytic reaction.

Furthermore, whether the nanostructured elements are unixially oriented or randomly oriented, it is preferred that at least one point of each nanostructured element must contact a two-dimensional surface common to all of the nanostructured elements.

The encapsulant is such that it can be applied to the exposed surface of the nanostructured elements in a liquid or liquid-like state, which can then be solidified or polymerized. The encapsulant may be in a vapor or vapor-like state that can be applied to the exposed surface of the nanostructured elements. Alternatively, the encapsulant is a solid or solid-like material, preferably powder or powder-like, which can be applied to the exposed surface of the nanostructured layer, transformed (e.g., by heating) to a liquid or liquid-like state (without adversely affecting the nanostructured layer composite), and then resolidified.

Organic encapsulants include polymers and co-polymers and include, for example, polymers derived from olefins and other vinyl monomers, condensation polymers, such as polyesters, polyimides, polyamides, polyethers, polyurethanes, polyureas, and natural polymers and their derivatives such as, cellulose, cellulose nitrate, gelatins, proteins, and natural and synthetic rubbers. Inorganic encapsulants that would be suitable, include for example, gels, sols, semiconductors, or metal oxides applied by, for example, vacuum processes. Preferably, the thickness of the encapsulant is in the range from about 1 $\mu$m to about 1 cm, and more preferably in the range from about 25 $\mu$m to about 2 mm.

The encapsulant may be applied to the nanostructured elements by means appropriate for the particular encapsulant. For example, an encapsulant in a liquid or liquid-like state may be applied to the exposed surface of the nanostructured elements by dip coating, vapor condensation, spray coating, roll coating, knife coating, or blade coating or any other art known coating method. An encapsulant may be applied in a vapor or vapor-like state by using conventional vapor deposition techniques including, for example, vacuum vapor deposition, chemical vapor deposition, or plasma vapor deposition.

An encapsulant that is solid or solid-like may be applied to the exposed surface of the nanostructured elements when liquified by application of a sufficient amount of energy, for example, by conduction or radiation heating to transform the solid or solid-like material to a liquid or liquid-like material, and then solidifying the liquid or liquid-like material. Alternatively, the nanostructured elements may be embedded into a solid or solid-like encapsulant by hot-roll calendering, that is using heat and pressure with a force sufficient to embed the nanostructured elements into the solid encapsulant, but without damaging the nanostructured elements.

The applied encapsulant, if liquid or in a liquid-like state, may be solidified by means appropriate to the particular material used. Such solidification means include, for example, curing or polymerizing techniques known in the art, including, for example, radiation, free radical, anionic, cationic, or step growth processes, and solvent evaporation, or combinations thereof. Other solidification means include, for example, freezing and gelling.

After the polymer is cured, the resulting nanostructured composite film of the present invention comprising nanostructured elements intimately encapsulated in an encapsulant is delaminated from the temporary substrate at the substrate:nanostructured element layer interface by mechanical means such as, for example, pulling the film from the temporary substrate, pulling the temporary substrate from the film, or both. In some instances, the film may self-delaminate during solidification of the encapsulant. Removal of the temporary substrate exposures the active surface of the nanostructured composite film.

Alternatively, the encapsulant can be a solid polymeric electrolyte. One example of such a solid polymer electrolyte is Nation ™ 117, a perfluorinated sulfonate ion exchange polymer commercially available in sheet form 0.028 cm thick or as a dilute solution, which can then be coated onto the nanostructured elements and then solidifed using art known techniques. Alternatively, an electrolyte can be mixed with a curable encapsulant and cured or the electrolyte can be incubated or allowed to permeate into a cured encapsulant. In contrast to the Nation ™ film, in these alternative forms the ionic element in the encapsulant is merely dissolved in the encapsulant, as opposed to being an integral part of the encapsulant's chemical structure.

Alternatively, a solventless process for embedding the nanostructured elements into a solid encapsulant can be used. Although applicable in concept to any nanostructured surface phase, that is, one comprising nanostructured elements of various material compositions, shapes, orientations, and packing densities the description of the process refers to the electrode membranes.

The nanostructured elements are hot pressed into the surface of the solid encapsulant by a calendering process, using controlled heat and pressure. For example, the nanostructured elements are brought into contact with the solid encapsulant at the nip part of a pair of heated rollers. The temporary substrate (from the nanostructured elements) is then stripped away, leaving the nanostructured elements penetrating the solid encapsulant that completely preserves their orientation and areal number density.

Placement of the nanostructured elements wholly within an electrolyte-containing encapsulant maximizes the catalyst electrolyte interface, and protects the elements from damage. Furthermore, having the elements coincident with the electrolyte-containing encapsulant surface optimizes the accessiblity of the analyte (gas or liquid consumed) to the catalyst/electrolyte three component interface. The discreteness of the nanostructured elements allows the surface electrode layer to remain permeable to the analyte, while the close packing of the elements assures the nanostructured composite films (NCF) remain electrically conducting as described in co-pending U.S. Pat. No. 5,238,729.

Alternative embodiments of this invention utilize the NCFs formed with the nanostructured elements encapsulated in a nonelectrolyte containing encapsulant, for use with liquid, paste (non-solid), or solid electrolytes. In this configuration, the nanostructured elements provide surface conductivity to the polymer and an electrochemically active surface in contact with the non-solid electrolytes while the encapsulant may function also as a diffusion limiting membrane (see FIGS. 4 and 5).

This invention is useful in electrochemical devices, such as gas, vapor and liquid sensors, fuel cells and batteries formed using the optimized electrode membrane construction.

Objects and advantages of this invention are further illustrated by the following examples, but the particular materials and amounts thereof recited in these examples, as well as other conditions and details, should not be construed to unduly limit this invention. All materials are commercially available or known to those skilled in the art unless otherwise stated or apparent.

EXAMPLES

Preparation of the Whiskers

In the following examples, nanostructured elements according to the present invention were prepared using processes described in U.S. Pat. Nos. 4,812,352 and 5,039,561 and such description is incorporated herein by reference.

Briefly, N,N'-di(3,5-xylyl)perylene-3,4:9,10 bis(dicarboximide), (hereinafter referred to as PR 149), was vacuum vapor deposited onto a flexible polyimide web, near room temperature, to a thickness on the order of 0.1 to 0.15 $\mu$m. Thereafter, the substrate and PR 149 coating were annealed in a vacuum sufficient to cause the initially uniform pigment film to convert to a highly nanostructured film. After annealing, the whiskers were discrete, uniformly oriented single crystals, 1 to 2 $\mu$m tall, with high aspect ratios (length to width), extremely large areal number densities (40–50/$\mu$m$^2$), and whisker to whisker spacings on the order of 0.05 $\mu$m. The resulting geometric surface area was increased by a factor of 10 to 15. The whiskers were then coated with a conducting material. The coated whiskers (nanostructured elements) were then embedded into the surface of a polymer to form a nanostructured composite film.

In the following examples, nanostructured composite films are demonstrated in two alternative embodiments, using two modes of operation, and in both two and three electrode configurations (see FIGS. 2–5). Electrodes of the nanostructured composite films can take the form of electrode membranes wherein the conducting coated whiskers are embedded in a permeable polymer membrane which is then placed in contact with the electrolyte (Examples 6–24), or the nanostructured elements may be placed directly within the surface of a solid polymer electrolyte (Examples 1–5 and 25). The sensors may be operated in both a potentiometric (open circuit EMF measurement) or amperometric mode. The amperometric mode can be of either a two or three electrode (potentiostat controlled) configuration.

EXAMPLE 1

This first example demonstrates the nanostructured composite films as high surface area electrodes embedded within the near surface region of a solid polymer electrolyte.

The nanostructured elements were first constructed as described above producing discrete, oriented whiskers, 1–2 $\mu$m in length on a Cu-coated polyimide temporary substrate. The whiskers were then coated with a mass equivalent thickness of 175 nm Pd by vacuum evaporation to produce nanostructured elements. A curable solid polymer electrolyte formulation consisting of 0.45 gram lithium perchlorate (LiClO$_4$) in 1 ml tetrahydrofuran (THF), 0.75 ml catalyst solution consisting of 25 $\mu$l dibutyl tin dilaurate in 10 ml THF, 1.5 ml 600 molecular weight poly(ethylene glycol) and 1.5 ml Desmodur TM N100 (Farbenfabriken Bayer AG) multifunctional isocyanate.

The sensor was made as follows: Approximately 0.1 ml of the curable solid polymer electrolyte solution was placed between two 10 mm diameter discs cut from the temporary substrate supporting the nanostructured elements. The sample was cured at approximately 40° C. for a period of about one hour. The temporary substrate of the nanostructured elements was then peeled away from the cured solid polymer electrolyte leaving the fresh, Pd-coated nanostructured electrodes embedded in the surface (catalytically active surface) of each side of the solid electrolyte disc (see FIG. 2). Electrical contact to both sides of the nanostructured electrode membrane was made using 0.3 mm diameter copper wire adhered to the electrode membrane with a trace amount of conducting silver paint (GC Electronics, Rockford, Ill.). One side of the membrane (counter electrode) was then isolated by coveting the entire surface with a 10 mm diameter piece of vinyl plastic electrical tape (commercially available from 3M).

The sensor was then exposed to 10 ppm hydrogen sulfide (H$_2$S) at approximately 10% relative humidity. The 10 ppm H$_2$S stream was generated by the addition of 0.2 liters per minute from a compressed air tank containing 500 ppm H$_2$S (Oxygen Services Company, St. Paul, Minn.) to 10 liters per minute (1/min.) air having 10% relative humidity. Exposure to the gas caused the sensor to generate an amperometric current signal. This resulting current signal was monitored with a Keithley 197A electrometer. A rapid response time of less than one minute to reach a steady state current of 0.1 $\mu$A with a signal to noise ratio of approximately 100 was observed. This corresponds to a sensitivity on a unit concentration, unit area basis of 0.013 $\mu$A ppm$^{-1}$ cm$^{-2}$. Upon removal of the hydrogen sulfide stream, the Sensor showed a rapid (<1 minute) reversible recovery to the original baseline (as measured with 10% relative humidity air).

EXAMPLES 2–5

Examples 2–4 describe a 3-electrode sensor comprising a working, counter and reference electrode membranes fabricated from nanostructured elements pressed directly into a solid polymer electrolyte. Example 5 describes a 2-electrode sensor comprising working and counter electrode membranes fabricated from nanostructured elements pressed directly into a solid polymer electrolyte. These examples show that compared to art known sensors made with metal mesh-powders/Nafion TM or metal grid/Nafion TM film electrodes, the nanostructured electrode membranes/Nafion TM film sensors show 50 to 100 times the response to NO$_2$ and H$_2$S in units of microamps per ppm ($\mu$A/ppm) of gas per unit planar area of working electrode.

The nanostructured composite film (NCF) based electrochemical sensor electrodes show measured gain factors of 50 to 100. They consist of oriented, metal coated organic whiskers, pressed into the surface of Nation TM film, or otherwise encapsulated in the surface of an SPE. The particles are ~2 $\mu$m long, ~0.05 $\mu$m in diameter, and have packing densities ~3-4×10$^9$/cm$^2$, which with relatively small amounts of metal coating thicknesses makes the composite surface conductive. The BET N$_2$ surface area enhancement factor for these whiskers with Pt-sputtered onto them to form "nanoscopically" "lumpy" conformal coatings have been measured to be ~3000. Part of this factor appears to be due to the 10-15 fold increase in surface area due simply to the geometric surface area increase, implying that the surface area increase due to the nanoscopic structure of the Pt on the whiskers is approximately 200. In contrast, a surface roughness factor of $\gamma$~1.4 is a given characteristic for bulk-like "bright" gold in Opekar (1992).

EXAMPLE 2

The nanostructured composite film having discrete, oriented whiskers on a Cu-coated polyimide temporary substrate was grown as described above. The working electrode membrane was constructed by coating $\leq 1$ $\mu$m tall whiskers with a mass equivalent thickness of 200 nm of Au by vacuum evaporation to produce catalytically coated whiskers. The counter and reference electrode membranes were constructed from nanostructured elements of 200 nm Pt vacuum evaporated onto whiskers 1-2 $\mu$m tall. Nation TM 117 film (commercially available from Dupont) was the solid polymer electrolyte (SPE) in this case.

The 3-electrode sensor was constructed from two 10 mm discs cut from the temporary substrate supporting the nanostructured elements (Au-coated and Pt-coated). The elements were pressed into a 1.5 cm by 3.5 cm piece of 0.028 cm thick Nation TM 117 film using a laboratory press (Fred S. Carver Inc., Wabash, Ind.) at a temperature of 149° C. and a force of 8,900 Newtons (1 ton) for a period of about 3 minutes. The configuration of the sensor (see FIG. 3) was such that the working electrode (Au-Coated elements) and the counter and reference electrodes (Pt-coated elements) were on opposing sides of the Nation TM 117 film, with the reference electrode directly behind the working electrode and the counter electrode to the side of the reference electrode. Electrical contact to the electrodes was made using 0.3 mm diameter Cu wire. The entire structure was encapsulated with vinyl plastic electrical tape. A 6 mm diameter opening was left in front of the working electrode, allowing exposure to the gas analyte.

Figure 6:
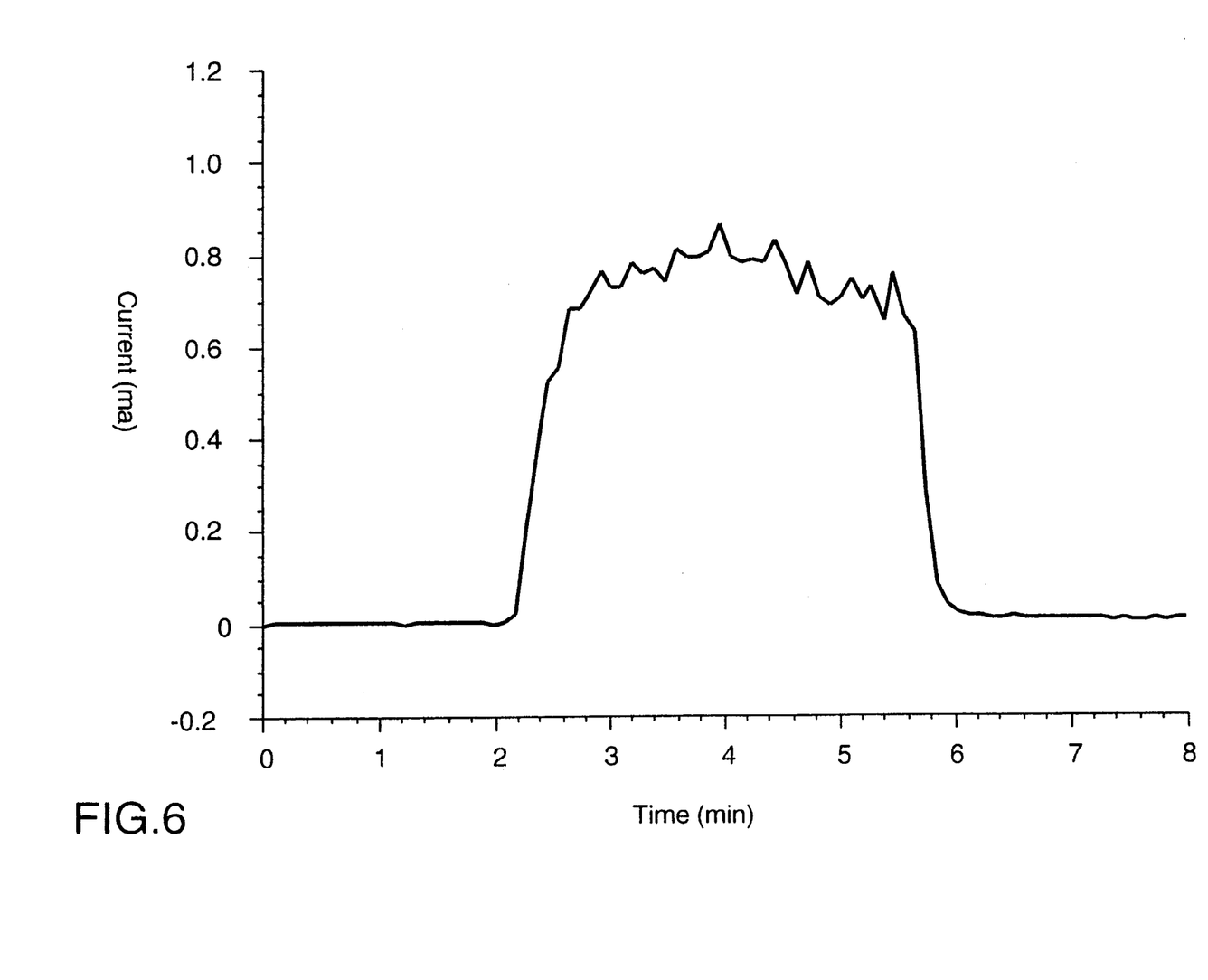
FIG. 6 is a graphical representation of current versus time for a sensor of the present invention.

A PAR model 273A potentiostat (EG & G Princeton Applied Research, Princeton, N.J.) was used to measure the resulting current on exposure to the gas analyte while maintaining a constant potential bias between the working and reference electrodes. In this example, the sensor was exposed to 200 ppm NO$_2$ at 78% relative humidity while maintaining a bias of $-0.3$ V between the working and reference electrode. The NO$_2$ stream was generated by adding 2 ml/min of pure NO$_2$ gas (Matheson, East Rutherford, N.J.) to 10 l/min air at 78% relative humidity and 23° C. The sensor response is shown in FIG. 6. The sensor gave a large, rapid response reaching a steady state current of 0.75 mA in approximately 1 minute. Upon removal of the NO$_2$, the sensor quickly returned to the baseline value with a recovery time of less than 1 minute. The magnitude of this signal corresponds to a sensitivity of 13.4 $\mu$A ppm$^{-1}$ cm$^{-2}$. This can be compared with a literature value (Opelcar 1992) of 0.26 $\mu$A ppm$^{-1}$ cm$^{-2}$ for a Au square grid pressed into the Nation TM 117 film as a working electrode under identical conditions of relative humidity and bias. By this example, use of the nanostructured electrode membrane of the present invention has improved the sensitivity by a factor of 51.5, or over 5000%.

EXAMPLE 3

In this example, a bias of $+0.3$ V was applied to the working electrode with respect to the reference, and the sample exposed to 200 ppm NO$_2$, all other conditions being equal to those in Example 2. In this case, a rapid, reversible response was again observed with a steady state signal of 0.14 mA. This corresponds to a sensitivity of 2.5 $\mu$A ppm$^{-1}$ cm$^{-2}$. This can be directly compared with a literature value of 0.024 $\mu$A ppm$^{-1}$ cm$^{-2}$ (Maclay et al., 1988) using a standard Au mesh-/Au powder working electrode under equivalent conditions. A factor of 104, or over 10,000%, improvement in sensitivity is obtained over the art known pressed electrode system.

EXAMPLE 4

In this example, the same sensor as in Examples 2 and 3 was exposed to a 10 ppm H$_2$S gas stream while maintaining a bias of $+0.3$ V between the working and reference electrode. The 10 ppm H$_2$S gas stream was generated by mixing 0.2 l/min of a 500 ppm H$_2$S compressed air cylinder (Oxygen Services) with 10 l/min air at 78% relative humidity and 23° C. A rapid, reversible response was observed with a steady state current of 79 $\mu$A. This corresponds to a sensitivity of 28 $\mu$A ppm$^{-1}$ cm$^{-2}$; a factor of 87.5 over a literature value (Maclay 1988) of 0.32 $\mu$A ppm$^{-1}$ cm$^{-2}$ for a standard Au mesh-/Au powder electrode under equivalent conditions.

EXAMPLE 5

Example 5 shows a nanostructured element/Nation TM 117 film construction that can be used as a potentiometric two electrode humidity sensor, particularly in inert gases, with both electrodes exposed to the same ambient.

A 2.5 cm square piece of Nation TM 117 membrane sheet, as used in Example 2, was formed into a two electrode sensor by hot platen pressing Au coated whiskers into one side of the sheet and NiCr-coated whiskers into the opposite side. Two samples of nanostructured whisker (1-1.5 $\mu$m tall) samples were prepared as described above, on a Cu-coated polyimide temporary substrate, and overcoated with sputter-deposited Au in one instance and sputter-deposited NiCr in the second. The planar equivalent thickness of the Au coating was on the order of 200 nm and that of the NiCr coating nominally 220 nm. The Au-coated nanostructured elements were placed with the elements against one side of the Nation TM 117 film piece. Both were sandwiched between larger sheets of 0.0048 cm thick polyimide (a processing aid used to protect the platens). The sandwich construction was pressed between the platens of the Carver Laboratory bench press for 15 seconds, with the platens maintained at a temperature of 138° C. and a total applied force of (two tons) 17,800 Newtons.

Figure 7:
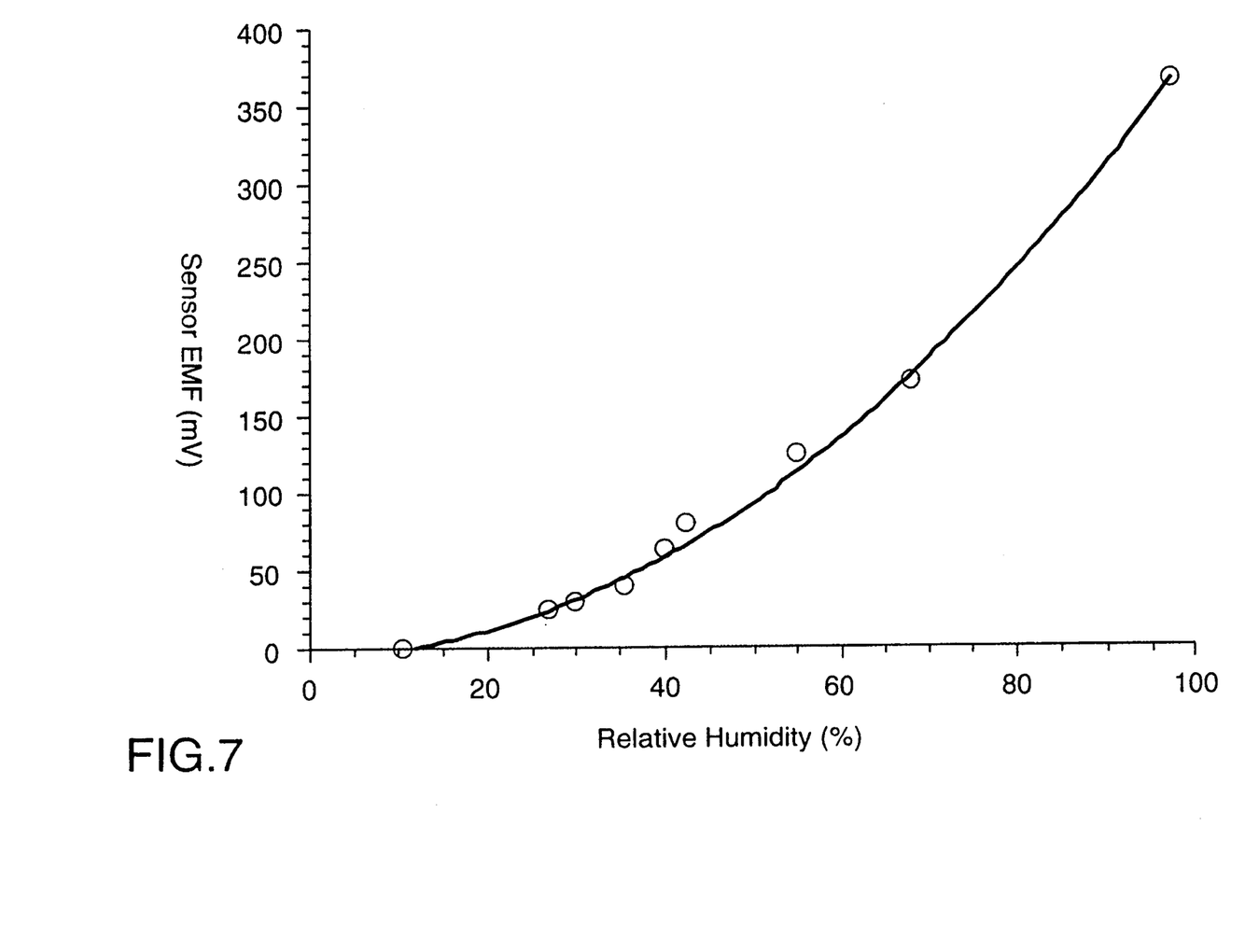
FIG. 7 is a graphical representation of EMF (mV) versus relative humidity for a sensor of the present invention.

After pressing, the temporary substrate peeled cleanly away from the Nation TM 117 film leaving the Au-coated whiskers embedded in the latter. This procedure was repeated, pressing for 20 seconds, to embed the NiCr-coated whiskers into the other side of the Nation TM 117 film piece. A 3 cm×1 cm strip was cut from the piece for testing. Electrical contact was made to each side of the strip with clip leads with only one jaw touching each respective side. An electromotive force (EMF) potential existed between the two leads with the sample in open air, the Au-coated side was positive with respect to the NiCr-coated side. The sample was then placed in a sealed container, with humidified $N_2$ flowing at 5 liters/min. The EMF was monitored with a chart recorder having an input impedance of 2.5 Mohm, as a function of the relative humidity (% RH) in the sealed container, measured with a General Eastern humidistat. The EMF was observed to vary nearly linearly between zero and 0.37 volts with %RH between 10% to 95%, as shown in FIG. 7.

EXAMPLES 6-24

Examples 6-24 describe an alternative construction wherein the nanostructured composite electrode is embedded in the surface of a permeable polymer film for the working electrode and a low permeability polymer film for the counter electrode (see FIG. 4). The sensors were produced by sandwiching an electrolyte paste between a working and counter electrode. The electrolyte paste was adjacent to the conductive surfaces of each nanostructured composite film.

Example 6 (Electrolyte A)

The membrane electrodes for this configuration were constructed by casting a 5 wt % solution of encapsulating polymer onto nanostructured elements consisting of a 175 nm thick Pd coating on PR 149 whiskers grown on the Cu-coated polyimide temporary substrate as described above. The encapsulating polymer for the working electrode was poly(trimethly silyl propyne) (PTMSP) (Huls Petrarch). The encapsulating polymer for the counter electrode was poly(ethyl methacrylate), a polymer with a lower permeability than PTMSP. The volume of encapsulating polymer solution provided a dried film approximately 0.1 mm thick.. After evaporation of the solvent, the nanostructured composite film was peeled away from the temporary substrate exposing the Pal-coated nanostructured elements at the surface of the nanostructured composite film. An electrolyte paste was prepared by adding 0.5 ml concentrated $H_2SO_4$ to 1 gram 100,000 molecular weight (MW) poly(ethylene oxide).

The sensor was then assembled in the following manner (see FIG. 4): Electrical contact was made to 10 mm diameter discs of the working and counter electrodes using 0.3 mm diameter copper wire adhered to the surface of the electrodes with a trace amount of silver paint (GC Electronics). A small, 6 mm inner diameter O-ring was filled with the electrolyte paste, and the two electrodes were then glued (3M CA-4 cyano acrylate adhesive) (exposure surfaces inward) to the perimeter of the O-ring leaving the nanostructured surface composite film to form an initimate contact with the electrolyte paste.

To measure the sensor response, a 100 K Ω load resistor was connected between the sensor leads, and the voltage across the load resistor, resulting from the current signal, was monitored with a Keithley 197A electrometer. The sample was then exposed to 10 ppm $H_2S$ in 10% relative humidity air at 23° C. The $H_2S$ stream was generated by mixing 0.2 l/min of a 500 ppm $H_2S$/compressed air tank (Oxygen Services) to 10 l/min of 10% relative humidity air. A rapid, reversible response to the $H_2S$ was observed with a steady state voltage corresponding to 0.032 mV.

TABLE 1

Electrolyte Paste

| | |
|---|---|
| B | 0.25 gram $LiClO_4$ dissolved in 0.25 ml HPLC grade water added to 1 gram 100,000 MW poly(ethylene oxide) |
| C | 0.5 ml 85% $H_3PO_4$ added to 1 gram 100,000 MW poly(ethylene oxide) |
| D | 0.25 gram $C_6H_5SO_3H$ dissolved in 0.25 ml HPLC grade water added to 1 gram 100,000 MW poly(ethylene oxide) |
| E | 0.26 gram $NH_4Cl$ dissolved in 0.5 ml HPLC grade water added to 0.25 gram 100,000 MW poly(ethylene oxide) |

EXAMPLES 7-24

The electrodes and sensor construction for these examples were prepared as described in Example 6. The various electrolyte pastes used in the sensor constructions were as described above in Table 1. The sensors were evaluated with various gases. All the gases used were diluted to 10 ppm in air at 10% relative humidity, 23° C. and a flow rate of 10 l/min. The results are summarized below in Table 2.

TABLE 2

| Example | Electrolyte | Gas | Signal (mV) |
|---|---|---|---|
| 7 | B | $NO_2$ | 0.2 |
| 8 | B | $H_2S$ | 0.005 |
| 9 | B | $SO_2$ | 0.02 |
| 10 | B | $NH_4$ | 0.003 |
| 11 | B | $Cl_2$ | 0.048 |
| 12 | B | HCl | 0.086 |
| 13 | B | CO | 0.004 |
| 14 | C | $H_2S$ | 0.086 |
| 15 | C | $Cl_2$ | 0.008 |
| 16 | C | HCl | 0.008 |
| 17 | D | $H_2S$ | 0.012 |
| 18 | D | CO | 0.004 |
| 19 | D | $NO_2$ | 0.003 |
| 20 | E | $H_2S$ | 0.04 |
| 21 | E | $SO_2$ | 0.1 |
| 22 | E | $NH_4$ | 0.01 |
| 23 | E | CO | 0.002 |
| 24 | E | $Cl_2$ | 0.004 |

EXAMPLE 25

In this example, a sensor was constructed by incubating a cured polymer/electrode sample in a solution of electrolyte and subsequent removal of the solvent. The nanostructured elements were the same as those described in Example 1.

The curable polymer formulation was 2 grams of 2000 molecular weight poly(tetrahydrofuran) dissolved in 2 ml THF, 10 μl dibutyl tin laurate catalyst and 0.5 ml Desmadur TM N100 brand isocyanate. Approximately 0.1 ml of this solution was cured between two 10 mm diameter discs of the temporary substrate supporting the nanostructured elements for approximately one hour at 23° C. Upon removal of the temporary substrate, the dried and cured sample having the nanostructured elements on each face of the disc was incubated in a 5 wt % solution of LiClO4 in THF and allowed to dry. Electrical contact to the two electrodes was made using 0.3 mm diameter Cu wire, and the sensor was encapsulated with vinyl electrical tape leaving a 6 mm diameter hole in the electrical tape for exposure of the working electrode. The sample was exposed to 10 liters per minutes of 10 ppm $H_2S$ in air at 57% relative humidity and 23° C. producing a rapid (<1 minute), reversible response of 0.1 μA.

Various modifications and alterations of this invention will become apparent to those skilled in the art without departing from the scope and principles of this invention, and it should be understood that this invention is not to be unduly limited to the illustrative embodiments set forth hereinabove. All publications and patents are herein incorporated by reference to the same extent as if each individual publication or patent was specifically and individually indicated to be incorporated by reference.

We claim:

1. An electrochemical cell comprising:
   (a) a working electrode comprising a first encapsulant layer, having a first set of nanostructured elements embedded therein, wherein one end of each nanostructured element is embedded within the encapsulant layer and the other end of each nanostructured element is coincident with a first surface of the first encapsulant layer, such that the first surface is a conductive surface;
   (b) a counter electrode comprising a second encapsulant layer, having a second set of nanostructured elements embedded therein, wherein one end of each nanostructured element is embedded within the encapsulant layer and the other end of each nanostructured element is coincident with a first surface of the second encapsulant layer, such that the first surface is a conductive surface; and
   (c) at least one electrolyte [such that]provided the electrolyte is in intimate contact with the conductive surface of both sets of nanostructured elements of the working and counter electrodes.

2. The electrochemical cell according to claim 1, wherein both sets of nanostructured elements are sub-microscopic two-components structures comprised of whiskers coated with an electrically conductive material.

3. The electrochemical cell according to claim 1, wherein both sets of nanostructured elements are sub-microscopic one-component structures of an electrically conductive material.

4. The electrochemical cell according to claim 1, wherein the electrolyte is dissolved in either the first or the second encapsulants or both.

5. The electrochemical cell according to claim 1, wherein the first and second encapsulants are each a solid electrolyte.

6. The electrochemical cell according to claim 1, further comprising a reference electrode comprising a third encapsulant having a third set of nanostructured elements embedded therein.

7. The electrochemical cell according to claim 1, wherein the second encapsulant of the counter electrode has a low permeability to an analyte and the first encapsulant has a higher permeability to the analyte.

8. An analyte sensor comprising in sequential order:
   (a) a first nanostructured electrode membrane, wherein the membrane comprises a first set of nanostructured elements embedded in a first encapsulant and such membrane has an conductive surface and a nonconductive surface;
   (b) an electrolyte; and
   (c) a second nanostructured electrode membrane, wherein the membrane comprises a second set of nanostructured elements embedded in a second encapsulant and such membrane has an conductive surface and a nonconductive surface;
   wherein the conductive surfaces of the first and second membranes are in intimate contact with the electrolyte.

9. The analyte sensor according to claim 8, wherein at least one set of nanostructured elements are sub-microscopic, two-component structures comprised of whiskers coated with an electrically conductive material.

10. The analyte sensor according to claim 8, wherein at least one set of nanostructured elements are sub-microscopic one-component structures of an electrically conductive material.

11. The analyte sensor according to claim 8, wherein the electrolyte is a non-solid electrolyte.

12. The analyte sensor according to claim 8, wherein the electrolyte is a solid electrolyte.

13. The analyte sensor according to claim 8, wherein the first and second encapsulants have different permeabilities.

14. A nanostructured composite film comprising:
   (a) a plurality of nanostructured elements, wherein the nanostructured elements are acicular, discrete, oriented, sub-microscopic, two-component structures comprised of whiskers coated with a conductive material; and
   (b) an encapsulant layer, wherein one end of each nanostructured element is embedded within the encapsulant layer and the other end of each nanostructured element is coincident with a first surface of the encapsulant layer, such that the first surface is a conductive surface.

15. The nanostructured composite film according to claim 14, wherein the whiskers are uniaxially oriented normal to the film surface.

16. The nanostructured composite film according to claim 14, wherein the catalytically active material is selected from the group consisting of conducting metals, semi-metals and semiconductors.

17. The nanostructured composite film according to claim 14, wherein the encapsulant is a solid electrolyte.

18. The nanostructured composite film according to claim 17, wherein the encapsulant is a perfluorinated sulfonate ion exchange polymer.

19. The nanostructured composite film according to claim 14, wherein an electrolyte is dissolved in the encapsulant.

20. A nanostructured electrode membrane comprising at least one set of nanostructured elements, wherein one end of each nanostructured element is embedded in a portion of an encapsulating solid electrolyte and the other end of each nanostructured element is coincident with a first surface of the encapsulating solid electrolyte.

21. The nanostructured electrode membrane according to claim 20, further comprising a second set of nanostructured elements embedded in an encapsulating solid electrolyte polymer, such that the first set and second set of nanostructured elements are on opposite surfaces of the encapsulating solid electrolyte polymer.

22. The nanostructured electrode membrane according to claim 21, wherein the first set of nanostructured elements are coated with a catalytically active material different from the catalytically active material of the second set of nanostructured elements.

23. The electrochemical cell according to claim 2 wherein the first set of nanostructured elements are coated with an electrically conductive material different from an electrically conductive material of the second set of nanostructured elements.

24. The nanostructured composite film according to claim 14 further comprising a plurality of nanostructured elements embedded in the surface opposite the first surface, such that both surfaces of the encapsulant layer are conductive surfaces.

25. The nanostructured electrode membrane according to claim 20 further comprising a second set of nanostructured elements embedded in a portion of the surface opposite the first surface, such that both surfaces of the encapsulating solid electrolyte are conductive surfaces.

26. The nanostructured electrode membrane according to claim 25 further comprising a third set of nanostructured elements embedded in either the first surface or the second surface of the encapsulating solid electrolyte, such that there are three conductive areas, with two conductive areas on the first surface and one conductive area on the second surface of the encapsulating solid electrolyte.

* * * * *

UNITED STATES PATENT AND TRADEMARK OFFICE
CERTIFICATE OF CORRECTION

PATENT NO. : 5,338,430

DATED : August 16, 1994

INVENTOR(S) : Parsonage et al

It is certified that error appears in the above-indentified patent and that said Letters Patent is hereby corrected as shown below:

Col. 1, line 37, Replace "an" with --art--

Col. 1, line 40, and throughout the patent; Do a global search and replace "Nation" with --Nafion--

Col. 3, line 59, Replace "Butther" with --Buttner--

Col. 4, line 48, Replace "$\leq$" with --$\leq$--

Col. 4, line 50, Replace "$\leq$" with --$\leq$--

Col. 4, line 66, Replace "$\geq$" with --$\geq$--

Col. 9, line 37, Replace "porphyfins" with --porphyrins--

UNITED STATES PATENT AND TRADEMARK OFFICE
CERTIFICATE OF CORRECTION

PATENT NO. : 5,338,430
DATED : August 16, 1994
INVENTOR(S) : Parsonage et al

It is certified that error appears in the above-indentified patent and that said Letters Patent is hereby corrected as shown below:

Col. 10, line 52, Replace "coveting" with --covering--

Col. 15, line 26, Replace "≤" with --≤--

Col. 16, line 4, Replace "Opelcar" with --Opekar--

Col. 17, line 46, Replace "Pat-coated" with --Pd-coated--

Col. 19, line 33, Delete "[such that"

Signed and Sealed this

Twentieth Day of December, 1994

Attest:

BRUCE LEHMAN

*Attesting Officer*  *Commissioner of Patents and Trademarks*